(12) United States Patent
Holmström

(10) Patent No.: US 6,447,670 B1
(45) Date of Patent: Sep. 10, 2002

(54) METHOD AND APPARATUS FOR COMPENSATING FOR DRIFT IN POTENTIAL OF A REFERENCE ELECTRODE IN ELECTROCHEMICAL MEASUREMENTS

(75) Inventor: Nils Holmström, Järfälla (SE)

(73) Assignee: Pacesetter AB, Järfälla (SE)

( * ) Notice: Subject to any disclaimer, the term of this patent is extended or adjusted under 35 U.S.C. 154(b) by 0 days.

(21) Appl. No.: 09/530,295

(22) PCT Filed: Oct. 20, 1998

(86) PCT No.: PCT/SE98/01876

§ 371 (c)(1),
(2), (4) Date: Jul. 11, 2000

(87) PCT Pub. No.: WO99/22232

PCT Pub. Date: May 6, 1999

(30) Foreign Application Priority Data

Oct. 29, 1997 (SE) ................................................ 9703957

(51) Int. Cl.$^7$ .............................................. G01N 27/26
(52) U.S. Cl. ...................... 205/775; 204/402; 204/412; 204/435
(58) Field of Search ................................ 204/412, 415, 204/402, 435, 431, 432; 205/775

(56) References Cited

U.S. PATENT DOCUMENTS 3,197,755 A  *  7/1965  Conger
3,260,656 A     7/1966  Ross, Jr.
4,269,684 A     5/1981  Zick
4,459,180 A  *  7/1984  Fogel
4,602,637 A     7/1986  Elmqvist et al.
4,611,604 A     9/1986  Botvidsson et al.
4,701,253 A    10/1987  Lightenberg et al.
4,779,618 A    10/1988  Mund et al.
4,853,091 A     8/1989  Mund et al.
5,562,815 A    10/1996  Preidel
5,985,129 A  * 11/1999  Gough et al.

* cited by examiner

Primary Examiner—T. Tung
(74) Attorney, Agent, or Firm—Schiff Hardin & Waite

(57) ABSTRACT

In a method and an apparatus for measuring a concentration of at least one dissolved chemical entity in a liquid medium, employing a counter electrode, a working electrode and a reference electrode immersed in the liquid medium, at least one measurement potential is applied to the working electrode relative to the reference electrode, corresponding to a measurement voltage during at least a part of a measurement period, thereby causing the dissolved chemical entity to participate in an electrochemical reaction at the working electrode, the chemical reaction resulting in a measurement evoked current. Compensation for potential drift at the reference electrode is achieved by comparing the measurement evoked current with a predetermined value, and decreasing or increasing the measurement voltage by an incremental value, in a negative or a positive incremental step, so that the measurement current approaches a predetermined value. After each increment, a new comparison is made and the next increment is determined dependent on that most recent comparison.

9 Claims, 5 Drawing Sheets

METHOD AND APPARATUS FOR COMPENSATING FOR DRIFT IN POTENTIAL OF A REFERENCE ELECTRODE IN ELECTROCHEMICAL MEASUREMENTS

BACKGROUND OF THE INVENTION

1. Field of the Invention

The present invention relates to a method for compensation of the potential drift of a reference electrode in electrochemical measurements of concentrations of at least one dissolved chemical entity in a liquid medium and also to an improved method for measuring the oxygen concentration in a liquid medium and an apparatus to be used with this method using a reference electrode, a working electrode and a counter electrode. The invention also relates to a pacemaker comprising an apparatus according to the invention and the use of a method according to the invention in a pacemaker or the like.

2. Description of the Prior Art

The terms listed below as used herein have the following definitions:

Measuring potential: the applied potential, as related to a reference potential, during the measurement, in the description denoted E.

Measuring voltage: used in algorithms denoted U, which are part of the present invention.

Floating potential: the potential, as related to a reference potential, an electrode will acquire when placed in an electrolyte and no current is allowed to pass through an outer circuit, i.e. not passing through the electrolyte, in the description denoted $E_0$.

It should be understood that these potentials actually refer to an arbitrarily chosen level, e.g. common ground.

Chemical entity: a chemical entity is defined for the purpose of this application as either a gas or a chemical substance or compound dissolved in a liquid medium.

Such entities can be subjected to analysis by electrolytic reduction/oxidation reactions and the corresponding reduction/oxidation potential, or rather the electric current evoked by said potentials for characterizing the amount and substance reduced/oxidized.

Working electrode: herein and below relates to the electrode at the surface of which the reduction of the chemical entity takes place.

Sensor rate: A calculated rate increase to be added to a basic pacing rate when the sensor is used in an active implant. The sensor herein and below being an oxygen sensor comprising a working electrode and a counter electrode and a reference electrode.

In modern medicine, implantable heart pacemakers are used increasingly for the therapy of heart arrhythmia. It is a well-known fact that physical demands on the body require levels of oxygen adapted to the degree of physical activity to be delivered to the body. Thus the body activity lowers the venous oxygen concentration in the blood as a function of the degree of activity. The oxygen concentration in the blood and the changes in the concentration may be used as indicators for a change in the stimulation pulse rate in order to regulate the rate of the stimulation pulses emitted by the pacemaker.

Oxygen in the blood exists in an equilibrium. The greater part of the oxygen is attached to the hemoglobin molecules while some part is dissolved in the blood plasma and transported thus through the vascular system including the heart. The amount of oxygen combining with the hemoglobin is dependent on the of oxygen partial pressure in the blood, measurements of either one will give indication as to the amount of oxygen present There are also other factors, which govern the ability of hemoglobin to combine with the oxygen, such as temperature and pH.

The oxygen saturation of the blood, which is a measure of the amount of oxygen bound by the hemoglobin, may be measured by different methods, e.g. transmission photometry and reflection photometry in the venous blood or measured indirectly by electrochemical methods, see above.

The photometric measurements do not show a linear dependency on the oxygen saturation and the measurement values have to be compensated in various ways, which is not the case in the electrochemical methods for measuring the oxygen partial pressure. In these latter methods there is a linear dependency in the measurements of the measured current as a function of the oxygen partial pressure.

The measurements using electro-chemical methods make use of the fact that the oxygen molecules dissolved in the blood are chemically reduced on the surface of the working electrode when the potential during a measurement pulse is forced to negative potential (about 1 volt) relative to a reference electrode/potential. The counter electrode is herein assumed, at least partly, to have a surface made from carbon. In the reduction process, hydroxide ions are produced and the amount of these ions are dependent on the concentration of dissolved oxygen according to the reactions:

at the working electrode 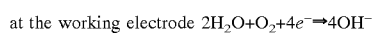

at the counter electrode 

The above equations show a simplified picture of the process in the liquid (electrolyte), but for the purpose of this description they are sufficient.

The electrical current flowing through the liquid medium to the working electrode during the measurement pulses is carried by the hydroxide ions. This current, called the oxygen current ($I_{pO2}$), is proportional to the amount of hydroxide ions formed on the surface. During the measurement pulse the carbon coating of the counter electrode is oxidized to minute amounts of carbon dioxide ($CO_2$), which is removed by the blood stream.

Patent documents disclosing different aspects of electrochemical measurement techniques are, e.g., U.S. Pat. Nos. 4,602,637 and 4,611,604 and 4,779,618 and 4,853,091. A factor influencing these measurements is the drift of the reference electrode.

One of the more stable reference electrodes that may be used is the Ag/AgCL-electrode. However, the biocompatibility of the reference electrode is important as the reference electrode is to be implanted. Other types of reference electrodes with better bio-compatibility are not as stable as the Ag/AgCl-electrode. The Ag/AgCl-electrode also must be protected by e.g. a membrane when used in vivo because of the above reason.

SUMMARY OF THE INVENTION

It is an object of the present invention to improve the stability and sensitivity of an apparatus and a method for making electrochemical measurements by diminishing the effects of the drift of the reference electrode.

Another object of the invention is to increase the overall sensitivity of the measurements.

Another object is to minimize the variations in the amplitude of the measuring current so as to maximize the sensitivity and to diminish possible side effects from currents rising above a certain limit.

Yet another object is reduce as much as possible the amount of energy used for the measuring pulses and still make certain that a relevant value is attained.

The above objects are achieved in accordance with the principles of the present invention in a method and an apparatus for making electrochemical measurements of a concentration of at least one dissolved chemical entity in a liquid medium, employing a counter electrode, a working electrode, and a reference electrode, wherein a measurement potential is applied to the working electrode relative to the reference electrode, corresponding to a measurement voltage, during at least a portion of a measurement period, at which time the dissolved chemical entity participates in an electrochemical reaction at the working electrode resulting in a measurement evoked current, and wherein the measurement evoked current is compared with a predetermined value, and the measurement voltage is decreased or increased in incremental steps so that the measurement current approaches the predetermined value, with the incremental steps being determined by successive comparisons between the successively measured evoked current and the predetermined value.

The invention is based on the observation that during testing of electrodes the measured oxygen current (the current arising as a result of the voltage imposed between the working electrode and the counter electrode) increases or decreases by time. It can, however, be shown that there is an optimal measurement potential where the relative sensitivity is the highest and which decreases on both sides of that optimum.

When the current decreases the sensitivity also decreases because the measurement potential comes closer to the limit beyond which the reduction no longer takes place. On the other hand if the current increases over time the measurement pulse amplitude will have to be reduced since otherwise the risk for tissue stimulation is obvious.

Thus, by continuously adjusting the measurement pulse amplitude compared to the so called reference electrode such that the measurement current $I_{pO2}$ approaches the predetermined value $I_{set}$. Experience from pre-clinical tests has shown that for e.g. a 7 mm² gold working electrode the measured oxygen current $I_{pO2}$ should be about 30–80 μA, depending on the area etc. of the working electrode, which will give the optimal results for this material.

The inventive method and the apparatus have several benefits. By keeping the current close to a set value, e.g. in the case of the oxygen-blood system 50 μA, it will be possible to obtain the best sensitivity in the measurements, i.e. the highest variation in the measured current as a function of the physical activity as related to rest.

DESCRIPTION OF THE PREFERRED EMBODIMENTS

The two diagrams in FIG. 1a and 1b will be further discussed below

Figure 3:
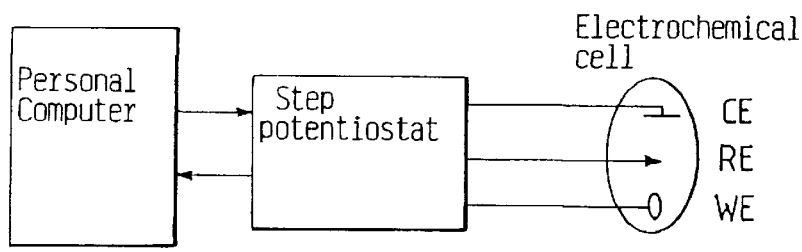
FIG. 3 is a schematic block diagram showing the basic components of a test system constructed and operating in accordance with the principles of the present invention.

To simulate the measurements according to the method of the invention and the use of an apparatus according to the invention and to show the relation between the current densities and sensitivity in measurements, a cell having a working electrode WE and a counter electrode CE was placed in a physiological saline solution. A mixture of 6% $O_2$, 6% $CO_2$ and 88% $N_2$ was bubble through the mixture to simulate the amount of oxygen solved in the blood at rest and 2% $O_2$, 6% $CO_2$ and 92% $N_2$ to simulate the amount during hard physical activity. The set up is shown in FIG. 3. The main components are a personal computer, or the like, with a two-way communication with a potential step potentiostat, which in turn co-acts with an electrochemical cell containing a fluid medium and, immersed into the cell, a working electrode WE (smooth pyrolytic carbon, having an area of 9 mm²), a reference electrode RE (e.g. an Ag/AgCl-electrode) and a counter electrode CE. The measurements were controlled by the personal computer.

It should be noted that the system is free-floating between the measurements. The variation in the sensitivity of the measurements and the current density in A/m² vs. the impressed potential on the working electrode as related to the reference electrode, the reference electrode RE in this case being a Ag/AgCl electrode, is shown in the diagrams in FIG. 2. The reason for chosing the current density as the variable in the above diagram is that the values shown, then will be independent of the area of the reference electrode and different electrodes may thus be compared to each other.

Figure 2:
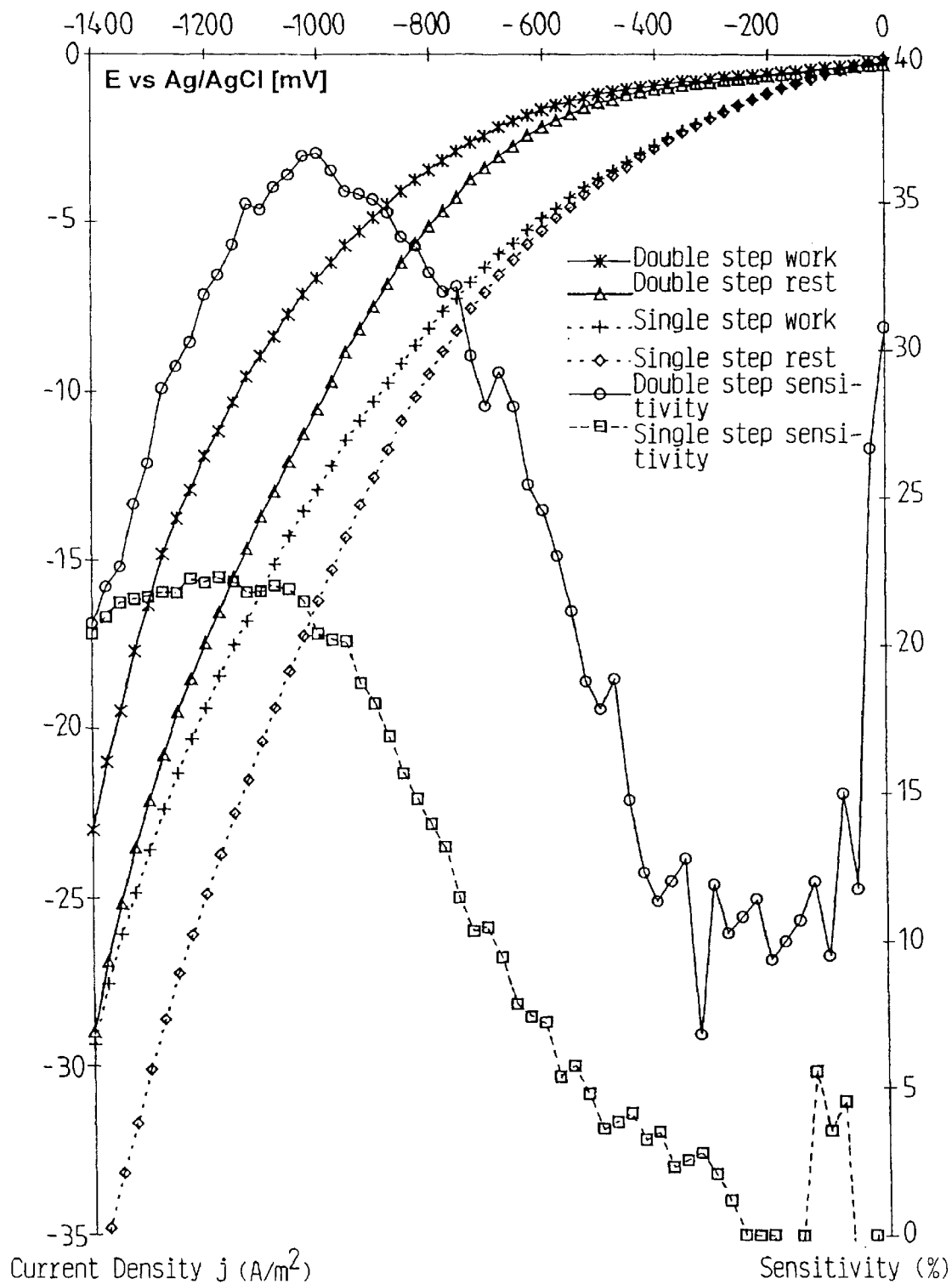
FIG. 2 shows curves relating the current density through the medium and the oxygen sensitivity to the measurement pulse potential.

In the diagram in FIG. 2 is given the respective curves for the current density with reference to the measurement voltage U both at rest and activity for a measurement series taken using a single step pulse and for a series of measurement using a double step pulse where in the later compensation for the double layer capacitance has been applied. FIG. 2 also shows the calculated sensitivity curves for measurements using a double step pulse with compensation denoted - - o - - and for measurements using a single step pulse - - □ - - . The sensitivity curve indicates the difference between the current density at work and at rest in % of the current density at rest. From the step curves it can be seen that the sensitivity curve for the double step pulse with compensation shows a higher sensitivity than that from the use of single step pulse without compensation. It also may be seen by comparison of the curves representing rest and the curve representing activity that, when the respective measurement curves for the two methods, single step without compensation and double step with compensation, respectively, for U having small values are compared, the curves at first follow each other closely and with an increasing U the gap between the two curves widens to a maximum and thereafter the gap shows a tendency to essentially remain constant as the current density increases.

The above measurements illustrate the sensitivity peak and the influence thereon from two different types of measurement pulses.

The method according to the invention is described with reference to two different flow-sheets describing two embodiments of the method.

It should be appreciated that the two embodiments may be each be combined with the two types of measurement pulses described in connection with FIGS. 1a and 1b, which are discussed below.

Figure 4A:
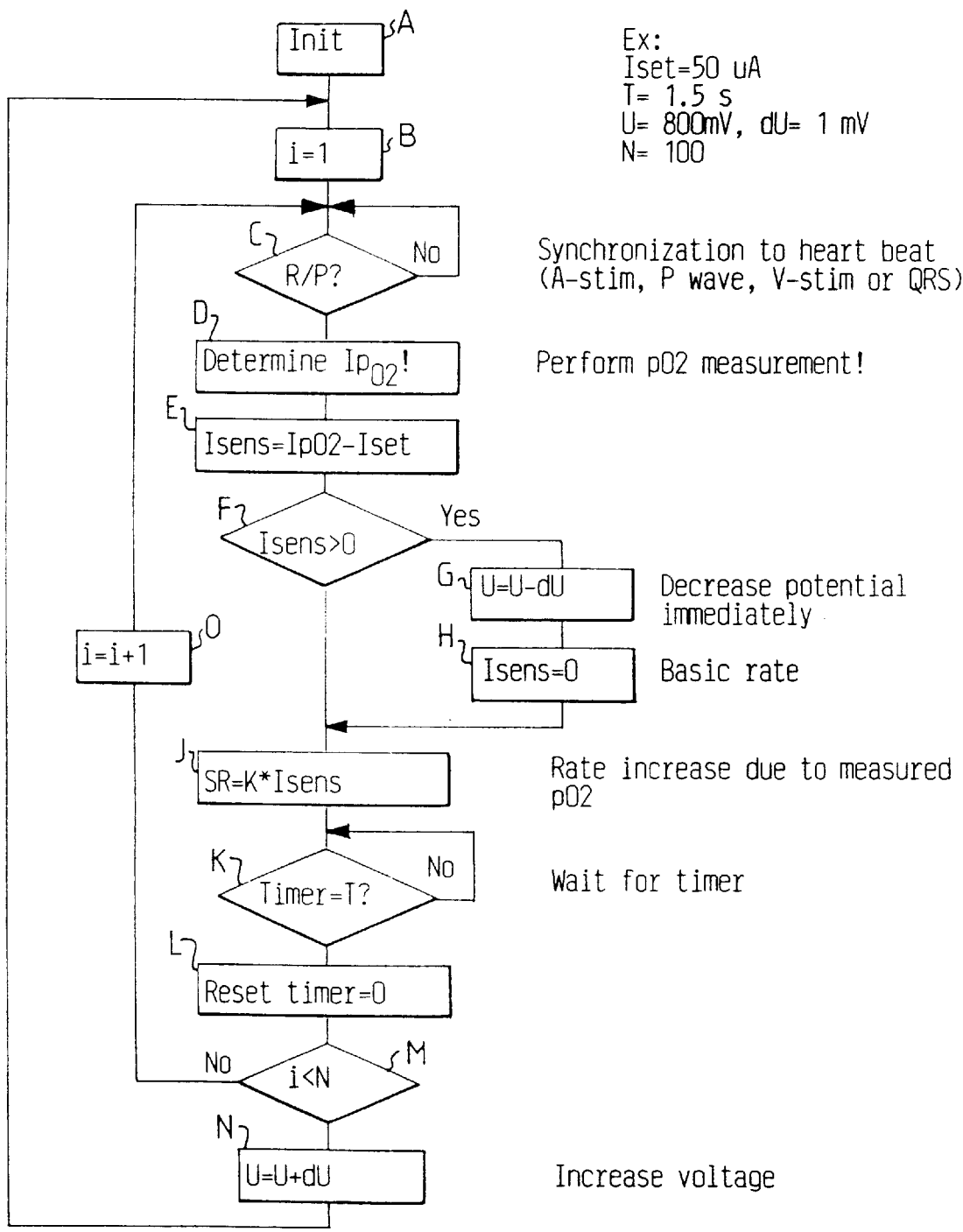
FIG. 4a and FIG. 4b each represents a flow chart for explaining the inventive method.

The first method described in the flow-sheet in FIG. 4a makes use of a set of initial values as follows:

In block A of FIG. 4a the initial values are set. The measurement voltage U is chosen to correspond a current $I_{set}$=50 µA, e.g. 800 mV, a time between measurements T=1.5 sec., an incremental step to be applied to the measuring potential dU=1 mV and a set number of cycles to be run through N=100 before the measurement cycle is restarted. The value of dU in the two instances where it is used in the algorithm could of course be set as two separate values $dU_1$ and $dU_2$.

In block B a counter "i" is set to "1".

Decision box C represents a waiting loop used for synchronizing the measurements to some event in the heart, e.g. an a trial or a ventricular stimulation pulse, a P-wave or a QRS-complex, for the measurements. The loop through decision box C is executed until "R/P?" is set to "TRUE", i.e. the specified event has occurred. At this point the $I_{pO2}$, i.e. the oxygen dependent current arising from the reaction of the oxygen at the working electrode WE, is determined by applying the measurement potential E (block D).

In block E a value $I_{sens}$ is calculated as $I_{sens}=I_{pO2}(i)-I_{set}$.

In decision box F it is checked if this value $I_{sens}$>0. If this is the case the applied measurement voltage is decreased immediately with a value dU in block G and $I_{sens}$ is set to "0" in block H.

In block J a rate increase SR (Sensor Rate) dependent on the measured $pO_2$ is set according to the formula SR=−K*$I_{sens}$. K may be a variable, programmable or a set value.

In decision box K a test is made "Timer=T?". If it is not the decision box is executed until the value of "Timer=T?" is "TRUE" and then in block L the timer is reset to "0".

In decision box M it is then tested if "i<N". If it is "TRUE" the value of "i" is increased by "1" in block O and return is made to decision box C.

Returning to decision box M, if the value of "i<N" is "FALSE" an increase of the measurement potential U is made with an increment of dU. Thereafter the procedure starts again in block B where "i" is set to "1".

The reason why loops therefore C-M, O, C to are executed a set number of times N before an increase is made in the measuring voltage U is to attain a slow adaptation of the $I_{pO2}$ to $I_{set}$. If the adaptation were to take place immediately there would hardly be any difference in the value $I_{sens}$ determined from cycle to cycle and thus no possibility to determine an increase in SR in block J.

The above implies that, if the oxygen content of the blood decreases due to e.g. exercise, the oxygen dependent current $I_{pO2}$ decreases, and $I_{sens}$ decreases, and the rate is set accordingly. If, on the other hand, the oxygen dependent current is increasing above $I_{set}$ due to e.g. drift of the reference electrode, a fast adaptation of the measuring potential U is effected. After N cycles an increased measurement potential is used which in turn will be rapidly adjusted downwardly if indicated by the next measurement.

In a second method a average value for $I_{pO2}$, being the measured current at each measurement, is calculated at the end of the N number of cycles. This is not done in the method according to FIG. 4a.

Figure 4B:
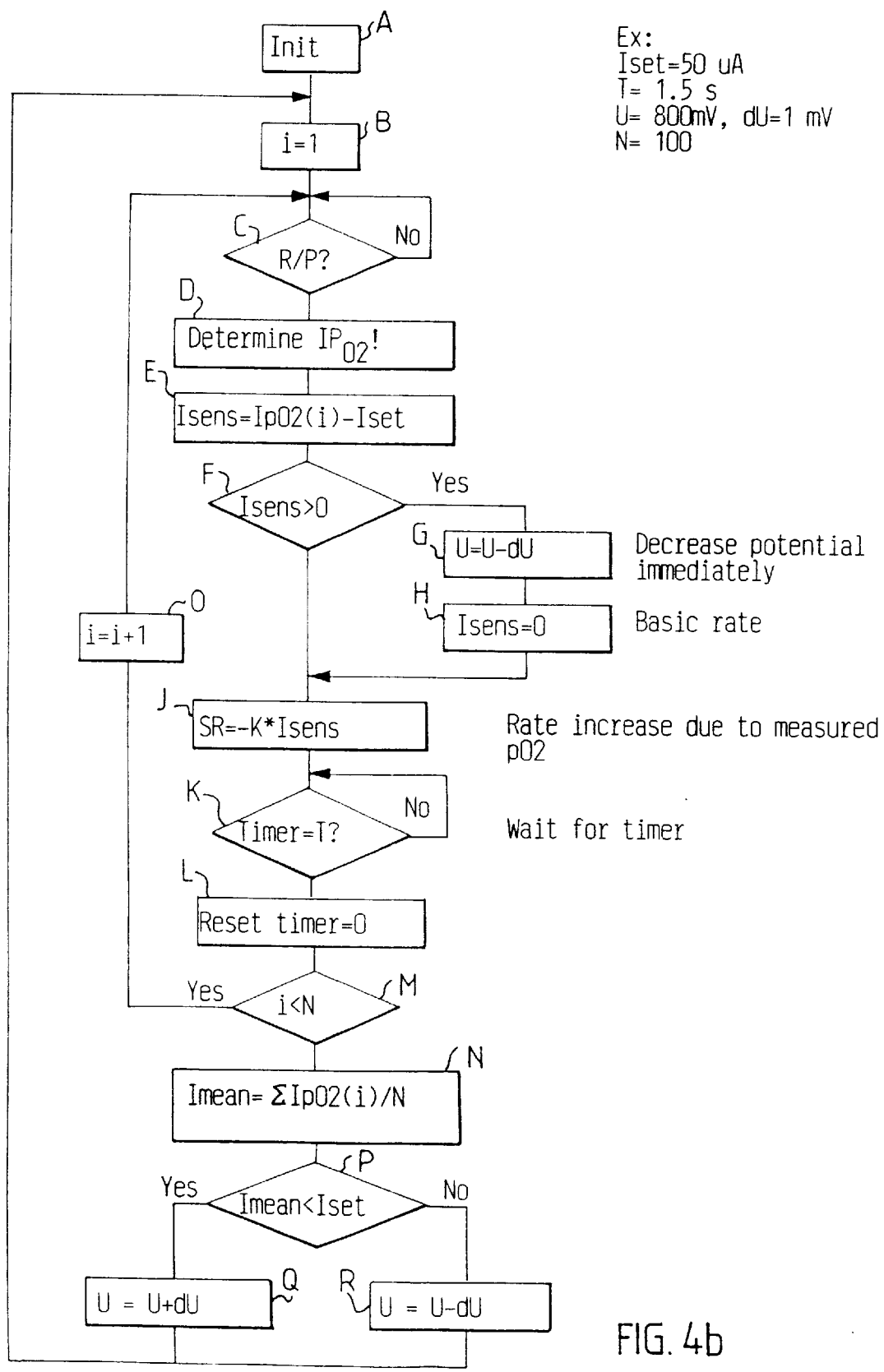

The second method described in the flow-sheet in FIG. 4b likewise makes use of a set of initial values as follows:

In block A of FIG. 4b the initial values are set. The measurement pulse is adjusted to give a current $I_{set}$=50 µA, a time between measurements T=1.5 sec., an incremental step to be applied to the measuring potential dU=1 mV and a set number of cycles to be executed N=100 before the measurement cycle is restarted.

The value of dU, which is used in three instances in the algorithm could of course be set as three different values, on for each instance, $dU_1$, $dU_2$, and $dU_3$.

In block B a counter "I" is set to "1".

Decision box C represents a waiting loop used for synchronizing the measurements to some event in the heart, e.g. an atrial or a ventricular stimulation pulse, a P-wave or a QRS-complex, for the measurements. The loop through decision box C is executed until "R/P?" is set to "TRUE", i.e. the specified event has occurred. At this point the measurement of the $I_{pO2}(i)$, i.e. the oxygen dependent current arising from the reaction of the oxygen at the working electrode WE, is performed by applying the measurement potential U in block D.

In block E a value $I_{sens}$ is calculated as $I_{sens}=I_{pO2}(i)-I_{set}$.

In decision box F it is checked if this value $I_{sens}$>0. If this is "TRUE" the applied measurement potential is decreased immediately with a value dU in block G and $I_{sens}$ is set to "0" in block H.

In block J a rate increase SR, dependent on the measured $I_{pO2}$, is set according to the formula SR=−K*$I_{sens}$. K may be a variable, programmable or a set value.

In decision box K a test is made "Timer=T?". If it is not the decision box is executed until the value of "Timer=T?" is "TRUE" and in block L the timer is reset to "0".

In decision box M it is then tested if "i<N". If this is "TRUE" the value of "i" is increased by "1" in block O and return is made to decision box C.

If the value of decision box M is "FALSE", a value $I_{mean}$ is calculated in block N according to the formula $I_{mean}=\Sigma I_{pO2}(i)/N$.

In decision box P the value $I_{mean}<I_{set}$ is checked. If it is "TRUE" U is increased in block Q with dU and if it is "FALSE" the value of U is decreased in block R with a value of dU.

After either of block R and block Q return is made to block B in which "i" is set to "1", and the measurement cycle is stared over again.

In the above algorithm consequently a check is made after a time T=the set value, e.g. 1.5 sec., as to the number of cycles N. If the number of cycles executed equals N a calculation of a value $I_{mean}=\Sigma I_{pO2}(i)/N$ is performed. A comparison thereafter made $I_{mean}<I_{set}$. If "TRUE" the measurement potential is increased with an amount dU and if "FALSE", a decrease of the measurement potential with an amount dU is made.

The above implies that, if the oxygen content of the blood is decreasing, the rate is increased accordingly. After N cycles the measurement potential is adjusted toward the value that gives a $I_{mean}=I_{set}$.

In a further embodiment of the methods described there is provided a possibility to vary the amount dU with which U is increased or decreased by making the value of dU a function of $I_{sens}$ in the measurements according to the methods described in connection with FIG. 4a and FIG. 4b.

In a preferred embodiment of the method according to the invention the results are used in an active implant such as a pacemaker or the like. The implant is preferably of the type which senses the heart activity and also paces the atrium and/or the ventricle. The rate adjustment provided for in the method according the invention is the used to control the implant, such that the pacing is adjusted continuously.

These above described methods can be performed in the form of a single measurement of the current during the measurement pulse. However, in order to compensate for especially the double layer capacitance of the electrode the preferred procedure is to integrate at least a part of the current caused by the measuring pulse over time and actually use this value for the control of the applied measurement potential. This will be described further in connection with the switching diagrams in FIG. 6.

Figure 5:
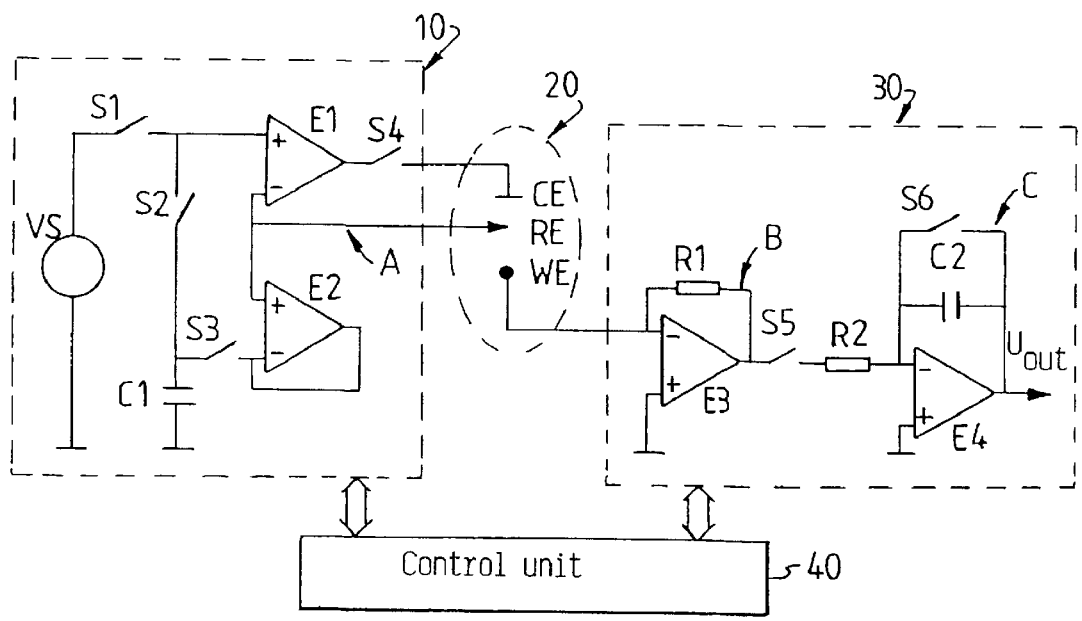
FIG. 5 is a circuit diagram of an apparatus operating according to the present invention.

A preferred device for accomplishing these measurements according to the algorithms in FIG. 4a and 4b, is shown in FIG. 5. The circuit diagram in FIG. 5 has three main parts. Part 10 includes the circuitry connected with the counter electrode CE and the reference electrode RE. Part 20 includes the liquid medium (the electrolyte) in which the counter electrode CE, and the reference electrode RE are immersed together with the working electrode WE. Part 30 comprises the circuitry connected to the working electrode WE. Part 30 also includes a current amplifier and an integrating circuit. A control unit 4b performs the steps of the method according the invention.

The control unit 40 includes among other things a microprocessor, a ROM in which a program implementing the invention for example in the form of the processes shown as examples in FIGS. 4a and 4b, may be stored, a RAM for storing and calculating data from the measurements and the calculations performed, input means, such as a programmable unit to be used in conjunction with a programmer (the programmer is a separate device used for communication with the active implant) in order to set initial values for the algorithm to be executed by the program, input channels for providing measurement data to the microprocessor, and A/D-converters for conversion of analog values measured in the process to serve as input data to the stored program, output channels from the microcomputer for sending control signals to control the measurements and to the various switches to be opened and closed during the different modes of the measurements.

When the device is implemented in a pacemaker as a part thereof, the programmable unit may be integrated in the control unit for controlling the pacing parameters. Also data channels for transfer of data such as P-wave etc. indications etc. may be provided in order to use these in e.g. the rate algorithm described.

Part 10 has a voltage source VS, the positive terminal of which is connected to a switch S1. The negative terminal of the voltage source VS is connected to a common ground. A capacitor C1 and a switch S2 are coupled together in series and are in parallel with the voltage source VS and the switch S1. The capacitor C1 is connected on one side to the common ground.

The non-inverting input of an operational amplifier E1 is connected to a point between the switches S1 and S2. The inverting input of the same amplifier E1 is coupled to the non-inverting input of an operational amplifier, coupled as a voltage follower E2. The output of the operational amplifier E1 is coupled via a switch S4 to the counter electrode CE. The reference electrode RE is coupled to a point between the inverting input of the said amplifier E1 and the non-inverting input of the amplifier E2.

The output of the operational amplifier E2 is thus coupled to the inverting input of E2 (voltage follower) and via switch S3, to a point between switch S2 and capacitor C1.

Part 20 contains the electrodes WE, CE and RE and the medium in which the measurements are to take place.

The working electrode WE is connected to the inverting input of a operational amplifier E3 in circuit part 30. The non-inverting input of the same is connected to the common ground. Parallel to the output of E3 and the inverting input of the same a resistor R1 (10 kΩ) is arranged. A switch S5 is connected in series to the resistor R2 (100 kΩ), which is coupled to the inverting input of E4. In the negative feedback loop of E4 the capacitor C2 and the switch S6 are connected in parallel.

The sample and hold circuit is formed by this last mentioned operational amplifier E4 having the inverting input connected to R2, the non-inverting input to the common ground and the switch S6 and the capacitor C2.

Figure 1A:
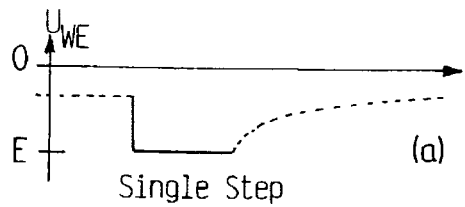
FIG. 1a shows a single step measuring pulse used in measurement in the inventive method and apparatus.
Figure 1B:
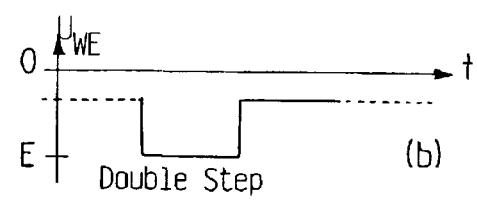
FIG. 1b shows a double step measuring pulse used in measurements in the inventive method and apparatus.

The two diagrams in FIGS. 1a and 1b each show the relationship of a controlled and a floating potential of the working electrode WE as related to the reference electrode RE vs. time. The dashed line signifies a free-floating state $E_0$ of the electrode when no current is flowing to the working electrode WE while the continuous lines represent the controlled potential E applied to WE during measurements. The type of pulse shown in FIG. 1a represents a single step pulse and in FIG. 1b a double step pulse for eliminating the influence of the double layer capacitance.

Figure 6:
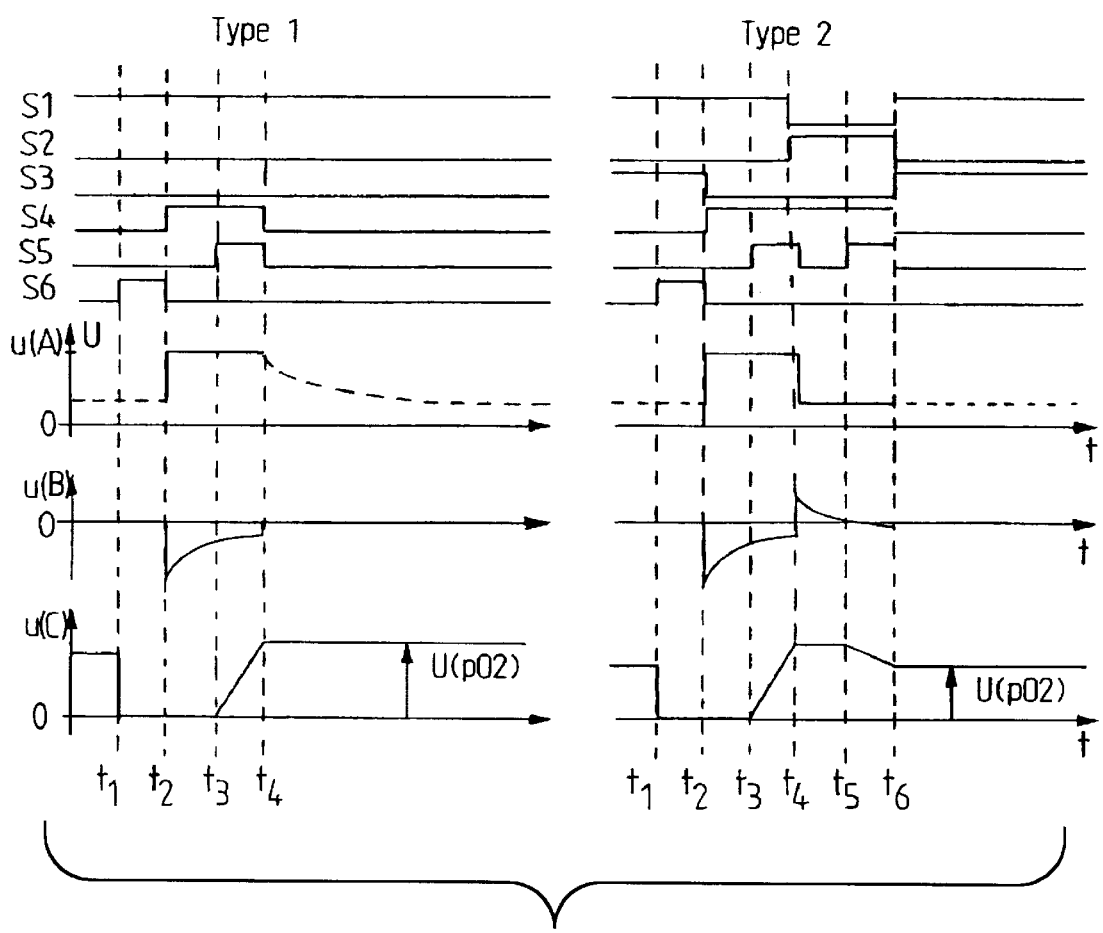
FIG. 6 illustrates switching which takes place in the device of FIG. 5, and also shows corresponding output voltages.

The switching diagram in FIG. 6 shows two variants (type 1 and type 2) of the switching modes for a measurement cycle of the device, and the resulting voltage on the output from the operational amplifiers in points A, B and C designated u(A), u(B), and u(C), respectively. The two switching diagrams correspond to the single step (type 1) and double step (type 2) measuring pulse shown in FIG. 1a and FIG. 1b.

The switching diagrams and the curves of the potentials in point A, B, and C are drawn to the same time-scale. It can thus be seen that in the single step (type 1) the measurements will be performed between $t=t_3$ and $t_4$, and in the double step (type 2) the measurements will be performed between $t=t_3$ and $t_4$, and between $t_5$ and $t_6$, and these measurements will be added on C2 in order to diminish the effects of the double layer.

The voltage source VS in FIG. 5 generates the desired measurement potential U. The value of U can be varied by a digital-analog-converter (DAC) controlled by a control unit. Just before the measurement pulse the integrating capacitor C2 is short-circuited by switch S6, C2 thus being reset.

To generate a type 1 single step pulse the switches S1, S2 and S3 are not changed (S1 is closed and S2, S3 are open all the time). When S4 is closed E1 will control its output so that its inputs are equal. Then the potential of the reference electrode will be the same as the voltage U. When S4 is open no current will flow through the electrochemical cell. The potential of the working electrode WE in this system will always have a potential equal to the common ground. This is a result of the current amplifier E3, which also gives an output voltage proportional to the measurement current due to u(B)=R1*I. (Note that in FIGS. 1a and 1b the potential of the working electrode WE is shown in relation to the reference electrode RE).

To generate a type 2 double step pulse the potential of the reference electrode just before the pulse is stored on capacitor C1. When the voltage follower E2, which charges C1 to the floating reference potential, is disconnected by switch S3, the voltage over C1 remains at that potential. At the first step the positive input of E1 is connected to the voltage source VS, at the second step it is connected to the capacitor C1. These two voltages are then sequentially imposed on the reference electrode.

In the diagrams denoted u(A), u(B) and u(C) in FIG. 6 the voltage at each instant is shown at the corresponding points (shown in FIG. 5). The voltage shown in point C is proportional to the oxygen current through the cell and may therefore be integrated over time to give the results in the form of an amount of electric charge.

After the measurement pulse the integrated current is held on the output of E4 to the next pulse:

$$u(C) = U(pO2) = \frac{R1}{C2*R2}\int I*dt.$$

This voltage $U(p_{O2})$ is fed back to the control unit, in which $I_{pO2}$ is calculated from u(C) and compared to the set current $I_{set}$.

It may be provided for in the algorithm used for controlling the measurements a possibility of stopping the sensor rate from rising to high, however this may also be provided by setting a maximum sensor rate in the pacemaker itself.

The invention has been described in connection with the process of sensing of oxygen in blood measurements, however there is a general principle involved in the method and device, which concerns the use of only three electrodes in this type of measurements and in which through the method of measurement and the described apparatus the influence of the drift in potential of the reference electrode is substantially diminished. This means that the invention as described generally applies to this type of measurements regardless of the substances involved. The rate adjustments which in the described application in used for adjusting the pacing rate of an active heart implant, a pacemaker or the like, could just as well in applications be used to regulate the addition of a substance or to adjust some parameter such as temperature in a temperature dependent reaction.

The method may be generally adapted to media other than blood as the liquid medium and to oxygen as the measured entity. The entity may also be represented by other gases in liquids and by chemicals dissolved in liquids. The apparatus as well may of course likewise be used for other media.

Although modifications and changes may be suggested by those skilled in the art, it is the intention of the inventor to embody within the patent warranted hereon all changes and modifications as reasonably and properly come within the scope of his contribution to the art.

I claim:

1. A method for making an electrochemical measurement of a concentration of at least one chemical entity dissolved in a liquid medium, comprising the steps of:

immersing only a counter electrode, a working electrode and a reference electrode in a liquid medium in which at least one chemical entity is dissolved;

applying a measurement potential to the working electrode relative to the reference electrode, corresponding to a measurement voltage during at least a portion of a measurement period, and thereby causing said chemical entity to participate in an electrochemical reaction at the working electrode, said electrochemical reaction resulting in a measurement evoked current;

measuring said measurement evoked current;

comparing said measurement evoked current with a predetermined value; and compensating for potential drift at said reference electrode by changing said measurement voltage in incremental steps to cause said measurement current to approach said predetermined value, and after each increment of said measurement voltage, comparing a resulting measurement evoked current with said predetermined value, and continuing incrementally changing said measurement potential until said measurement evoked current is substantially equal to said predetermined value.

2. A method as claimed in claim 1 comprising selecting each of said increments of said measurement potential from the group consisting of a positive increment and a negative increment, dependent on a difference formed by subtracting said predetermined value from said measurement evoked current, and decreasing said measurement potential when said difference is greater than zero and increasing said measurement potential after a predetermined number of increments.

3. A method as claimed in claim 1 comprising selecting each of said increments of said measurement potential from the group consisting of a positive increment and a negative increment, dependent on a difference formed by subtracting said predetermined value from said measurement evoked current, and decreasing said measurement potential when said difference is greater than zero and, after a predetermined number of increments, calculating an average value of said measurement evoked current and increasing said measurement potential if said average value is less than said predetermined value and decreasing said measurement potential if said average value is greater than or equal to said predetermined value.

4. A method as claimed in claim 1, wherein the step of immersing comprises immersing said counter electrode, said working electrode and said reference electrode in blood as said liquid medium, said blood having oxygen dissolved therein as said chemical entity.

5. A method as claimed in claim 1 comprising, before each measurement period, placing said working electrode in a free-floating potential state.

6. An apparatus for making an electrochemical measurement of a concentration of at least one chemical entity dissolved in a liquid medium, comprising:

only a counter electrode, a working electrode and a reference electrode immersed in a liquid medium in which at least one chemical entity is dissolved;

a potentiostat for applying a measurement potential to the working electrode relative to the reference electrode, corresponding to a measurement voltage during at least a portion of measurement period, and thereby causing said chemical entity to participate in an electrochemical reaction at the working electrode, said electrochemical reaction resulting in a measurement evoked current;

a measuring unit for said measurement evoked current;

a comparator for comparing said measurement evoked current with a predetermined value to obtain a comparison result; and said potentiostat compensating for potential drift at said reference electrode by changing said measurement voltage in incremental steps to cause said measurement current to approach said predetermined value, and after each increment of said measurement voltage, said comparator comparing a resulting measurement evoked current with said predetermined value and supplying said comparison result to said potentiostat, and said potentiostat continuing to incrementally change said measurement potential until said measurement evoked current is substantially equal to said predetermined value.

7. An apparatus as claimed in claim 6 wherein said liquid medium is blood and wherein said chemical entity is oxygen dissolved in blood, and further comprising electronic circuitry for administering electrical therapy to a subject dependent on said concentration.

8. An apparatus as claimed in claim 7 wherein said circuitry comprises circuitry for pacing a heart and for sensing cardiac functions, and for controlling application of said measurement potential to said working electrode dependent on said cardiac functions.

9. An apparatus as claimed in claim 7 wherein said circuitry comprises control circuitry for controlling administration of said therapy dependent on a difference obtained by subtracting said measurement evoked current from said predetermined value.

* * * * *